United States Patent [19]

Schmolka

[11] 4,359,478

[45] Nov. 16, 1982

[54] HYPOCHOLESTEROLAEMIC AGENTS

[75] Inventor: Irving R. Schmolka, Grosse Ile, Mich.

[73] Assignee: BASF Wyandotte Corporation, Wyandotte, Mich.

[21] Appl. No.: 283,691

[22] Filed: Jul. 15, 1981

[51] Int. Cl.³ .............................................. C07C 69/76
[52] U.S. Cl. ................................... 424/308; 424/299; 424/311; 560/112; 560/182; 560/189; 560/263
[58] Field of Search ............... 560/203, 112, 189, 182; 424/299, 308, 311

[56] References Cited

U.S. PATENT DOCUMENTS 3,067,222 12/1962 Anderson .......................... 560/263
4,243,799 1/1981 Mueller et al. ..................... 560/112

*Primary Examiner*—Paul J. Killos
*Attorney, Agent, or Firm*—Joseph D. Michaels

[57] ABSTRACT

Certain polyoxybutylene-polyoxyethylene block copolymers and their mono or diesters are useful in a diet as hypocholesterolaemic agents.

10 Claims, No Drawings

HYPOCHOLESTEROLAEMIC AGENTS

BACKGROUND OF THE INVENTION

1. Field of the Invention

Certain polyoxybutylene-polyoxyethylene block copolymers and their mono or diesters are useful in a diet to reduce the amount of cholesterol contained in the blood and serve as an anti-obesity agent by inhibiting intestinal lipid transport.

2. Description of the Prior Art

Arteriosclerosis and heart diseases have long been associated with higher than normal serum lipid levels, most notably cholesterol and triglycerides. U.S. Pat. No. 3,916,008 relates to the use of certain novel esters of a specific group of nonionic surfactants based on ethylene diamine and oxyethylene groups accounting for 0 to 30 percent of the total molecular weight and oxypropylene groups accounting for a molecular weight of from 2250 to 3250 to reduce blood serum lipid levels. U.S. Pat. No. 3,932,659 relates to methods for reducing serum cholesterol by oral administration of a polyoxypropylene-polyoxyethylene adduct of ethylene diamine having a partial molecular weight of the polyoxypropylene of about 2250-3250 and a polyoxyethylene content between 0 percent and 30 percent. It has now been found that certain block copolymers of butylene oxide and ethylene oxide and their esters, serve to inhibit high serum lipid levels when incorporated into the diet.

SUMMARY OF THE INVENTION

The invention relates to the use of certain polyoxybutylene-polyoxyethylene block copolymers and their mono or diesters as hypocholesterolaemic agents. The block copolymers are a cogeneric mixture of conjugated polyoxybutylene-polyoxyethylene compounds containing in their structure oxybutylene groups, oxyethylene groups and an organic radical derived from an organic compound containing a plurality of reactive hydrogen atoms, preferably a water-soluble organic compound containing a plurality of reactive hydrogen atoms and 2 to 12 carbon atoms; the compounds being characterized in that all the oxybutylene groups are present in polyoxybutylene chains that are attached to the organic radical at the site of a reactive hydrogen atom thereby principally constituting a polyoxybutylene polymer; the oxyethylene groups being attached to the polyoxybutylene polymer in polyoxyethylene chains; the average molecular weight of the polyoxybutylene polymers in the mixture being at least 600, as determined by hydroxyl number, and the oxyethylene groups present constituting 5 to 50 percent by weight of the compound.

DESCRIPTION OF THE PREFERRED EMBODIMENTS

The block copolymer of use in the invention is a cogeneric mixture of conjugated polyoxybutylene polyoxyethylene compounds having as a hydrophobe, a polyoxybutylene polymer of at least 600 molecular weight. The polyoxybutylene compounds are prepared by first condensing butylene oxide with an organic compound containing a plurality of reactive hydrogen atoms to prepare a polyoxybutylene polymer of at least 600 molecular weight, and subsequently condensing ethylene oxide thereto. The compounds used in this invention conform to the following generic formula:

$$Y[(C_4H_8O)_n\text{-}E\text{-}H]_x \qquad (A)$$

wherein Y is the residue of a water soluble organic compound containing therein x active hydrogen atoms; n is an integer; x is an integer greater than 1; the values of n and x are such that the molecular weight of the compound, exclusive of E, is at least 600 as determined by hydroxyl number; E is a polyoxyalkylene chain wehrein the oxygen/carbon atom ratio is at least 0.5, and E constitutes 5 percent by weight to 50 percent by weight of the compound.

The polyoxybutylene polymer, which is an intermediate in the preparation of the compounds of use in this invention, has the following structure:

$$Y[(C_4H_8O)_nH]_x \qquad (B)$$

wherein Y, n and x are defined as in Formula A above.

The preferred compounds of use in this invention are prepared by condensing ethylene oxide in an amount between 5 and 50 percent by weight of the resultant compound, with the polyoxybutylene polymer. These compounds have the following formula:

$$Y[(C_4H_8O)_n(C_2H_4O)_mH]_x \qquad (C)$$

wherein Y, n and x are defined as in Formula A and m has a value such that the oxyethylene groups constitute 5 to 50 percent by weight of the compound.

When ethylene oxide is condensed with a polyoxybutylene glycol of at least 600 molecular weight and derived from a butane diol initiator, the resulting compounds have the following structure:

$$HO(C_2H_4O)_m(C_4H_8O)_n(C_2H_4O)_{m'}H \qquad (D)$$

wherein n is defined as previously set forth; and $m'+m$ have a value such that the oxyethylene groups constitute 5 percent by weight to 50 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio contained therein is at least 0.5.

Examples of a water-soluble organic compound containing therein x active hydrogen atoms, the residue of which is Y, are the initiators which may include water; diols such as propane diol, butane diol, triols such as glycerol, tetrols such as pentaerythritol as well as initiators containing more than four hydroxyl groups such as hexitol or sucrose. Also, amines and other low molecular weight water-soluble compounds having two or more active hydrogen atoms such as ethylene diamine or diethylene triamine may be used as the initiator. Preferably used is butane diol. More preferably used is 1,4-butanediol.

The butylene oxide used in making the hydrophobic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the block copolymers used in this invention. In lieu of butylene oxide, methyloxetane, tetrahydrofuran and isobutylene oxide may be used.

The block copolymers of use in this invention conforming to structure D above, include those block copolymers which contain a hydrophobe of 600 approximate average molecular weight and an ethylene oxide content of from about 5 percent by weight to about 50 percent by weight of the total molecular weight of the unesterified polymers; a hydrophobe of up to a maximum of 4000 approximate average molecular weight and an ethylene oxide content of between about 5 and about 50 percent by weight of the total molecular weight of the unesterified polymer; preferably a hydrophobe of about 1200, 1800, 2400, 3,000, 3,600 or higher approximate average molecular weight and an ethylene oxide content of about 5 percent by weight to about 50 percent by weight of the total molecular weight of the unesterified polymer.

The mono and diesters of the block polymers of this invention may be prepared from any organic acid in an esterification process. The esters of use in this invention may be prepared by reacting the block copolymer of formula (D) above and a fatty acid chloride such as lauroyl chloride or benzoyl chloride in an amount of 1 to 2 moles of acid chloride per mole of block copolymer using standard techniques such as reacting at about 105° C. under reflux conditions and removing hydrochloric acid formed. The mono and diesters of block copolymers of formula (D) have the following formula:

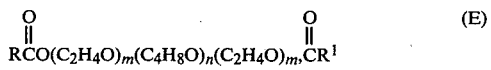

$$RCO(C_2H_4O)_m(C_4H_8O)_n(C_2H_4O)_{m'}CR^1 \quad (E)$$

wherein $m+m'$ and n are defined as previously set forth and R and $R^1$ are H or the residues of aliphatic, aromatic, amino aliphatic or amino aromatic acids, i.e., R and $R^1$ are H or alkyl, cycloalkyl, aryl, substituted aryl, aralkyl, substituted aralkyl, alkylamino or arylamino group, such as glycollic, citric, benzoic, acetic and hexanoic with the proviso that only one of R and $R^1$ may be H. Suitable esters are the glycolate, citrate, benzoate acetate, hexanoate, mono or diesters of the block copolymers mentioned above. The lipid inhibition of the block copolymers of this invention is unexpectedly superior to the prior art polyoxypropylene-polyoxyethylene block copolymers of comparable hydrophobe molecular weight.

A typical diet comprises from 15 to 25 parts protein, 25 to 65 parts carbohydrate, 10 to 30 parts fat, 0.2 to 1.5 parts choloresterol, about 9.5 parts minor additives, water, etc., about 10 parts neutral materials to which has been added about 0.1 to 2.0 parts hypocholesterolaemic agent of the invention.

Examples I and II below illustrate specific diet compositions within which the hypocholesterolaemic agents of the invention are effective.

EXAMPLE I

| Ingredients | Parts |
| --- | --- |
| Protein | 20.0 |
| Carbohydrate | 35.0 |
| Fat | 25.0 |
| Cholesterol | 0.5 |
| Block Copolymer A | 1.0 |
| Other Minor Additives, water, etc. | 9.5 |

Block copolymer A is a polyoxybutylene-polyoxyethylene block copolymer of an approximate average molecular weight of the polyoxybutylene hydrophobe of 1800 and an oxyethylene content of about 20 percent by weight of the block copolymer.

EXAMPLE II

| Ingredient | Parts |
| --- | --- |
| Protein | 15.0 |
| Carbohydrate | 50.0 |
| Fat | 15.0 |
| Cholesterol | 1.0 |
| Block Copolymer B | 0.5 |
| Other Minor Additives, water, etc. | 9.5 |

Block copolymer B is a polyoxybutylene-polyoxyethylene block copolymer of an approximate average molecular weight of the polyoxybutylene hydrophobe of 2400 and an oxyethylene content of about 20 percent by weight of the block copolymer.

EXAMPLE III

An ester of block copolymer A was prepared as follows: To 2 moles of benzoyl chloride are added 1 mole of block copolymer A, with stirring at a temperature of 105° C. under reflux conditions. The hydrochloric acid is removed, and after washing with dilute sodium bicarbonate and drying, the benzoic diester of block copolymer A is prepared. This diester is useful as a substitute for block copolymer A in the diet Example I.

The embodiments of the invention in which an exclusive privilege or property is claimed are defined as follows:

1. A compound of the formula:

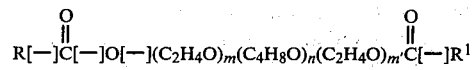

$$R[-]C[-]O[-](C_2H_4O)_m(C_4H_8O)_n(C_2H_4O)_{m'}C[-]R^1$$

wherein R and $R^1$ are H or the residue of an aliphatic, cycloaliphatic, or aromatic acid containing from 2 to 12 carbon atoms with the proviso that only one of R and $R^1$ may be H and $m+m'$ and n are integers such that the approximate average molecular weight of $(C_4H_8O)_n$, representing a polyoxybutylene hydrophobe is between 600 and 4000 and the content of $(C_2H_4O)_{m+m'}$, representing oxyethylene groups constitute about 5 to about 50 percent by weight of the compound.

2. The compound of claim 1 wherein the polyoxybutylene hydrophobe has an approximate average molecular weight of about 1200.

3. The compound of claim 1 wherein the polyoxybutylene hydrophobe has an approximate average molecular weight of about 1800.

4. The compound of claim 1 wherein the polyoxybutylene hydrophobe has an approximate average molecular weight of about 2400.

5. The compound of claim 1 wherein R and $R^1$ are H or the residue of glycollic, citric, benzoic, acetic or hexanoic acid with the proviso that only one of R and $R^1$ may be H.

6. A method for inhibiting the intestinal lipid transport of an animal or human being in need thereof, which comprises orally administering to such animal or human being an effective amount of a hypocholesterolaemic agent which is selected from the group consisting of (A) a polyoxybutylene-polyoxyethylene block copolymer, said block copolymer being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms, the compounds being characterized in that all the oxybutylene groups are present in polyoxybutylene chains that are attached to the organic radical at the site of a reactive hydrogen atom thereby principally constituting a polyoxybutylene polymer; the oxyethylene groups being attached to the polyoxybutylene polymer in polyoxyethylene chains; the approximate average molecular weight of the polyoxybutylene polymers in the mixture being between 600 and 4000, as determined by hydroxyl number, and the oxyethylene groups present constituting about 5 to about 50 percent by weight of the compound, and (B) a compound of the formula:

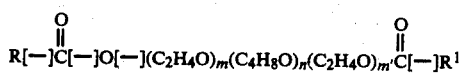

wherein R and $R^1$ are H or the residue of an aliphatic, cycloaliphatic, or aromatic acid containing from 2 to 12 carbon atoms with the proviso that only one of R and $R^1$ may be H and $m+m'$ and n are integers such that the approximate average molecular weight of $(C_4H_8O)_n$, representing a polyoxybutylene hydrophobe is between 600 and 4000 and the content of $(C_2H_4O)_{m+m'}$, representing oxyethylene groups constitute about 5 to about 50 percent by weight of the compound.

7. The method of claim 6 wherein the polyoxybutylene hydrophobe has an approximate average molecular weight of about 1200.

8. The method of claim 6 wherein the polyoxybutylene hydrophobe has an approximate average molecular weight of about 1800.

9. The method of claim 6 wherein the polyoxybutylene hydrophobe has an approximate average molecular weight of about 2400.

10. The method of claim 6 wherein R and $R^1$ are H or the residue of glycollic, citric, benzoic, acetic or hexanoic acid with the proviso that only one of R and $R^1$ may be H.

* * * * *